(12) United States Patent
Janusz et al.

(10) Patent No.: US 6,852,700 B1
(45) Date of Patent: Feb. 8, 2005

(54) COLOSTRININ, AND USES THEREOF

(75) Inventors: Marin Janusz, Wroclaw (PL); Jozef Lisowski, Wroclaw (PL); Anna Dubowska-Inglot, deceased, late of Wroclaw (PL); by Mieczyslaw Inglot, legal representative, Wroclaw (PL)

(73) Assignee: Ludwig Hirzfeld Institute of Immunology and Experimental Therapy, Polish Academy of Sciences, Warsaw (PL)

( * ) Notice: Subject to any disclaimer, the term of this patent is extended or adjusted under 35 U.S.C. 154(b) by 0 days.

(21) Appl. No.: 09/269,845

(22) PCT Filed: Oct. 3, 1997

(86) PCT No.: PCT/GB97/02721

§ 371 (c)(1),
(2), (4) Date: Sep. 24, 1999

(87) PCT Pub. No.: WO98/14473

PCT Pub. Date: Apr. 9, 1998

(30) Foreign Application Priority Data

Oct. 3, 1996  (PL) ................................................ 316416

(51) Int. Cl.[7] .............................................. A61K 31/70
(52) U.S. Cl. ............................... 514/21; 514/2; 514/12; 514/15; 530/300; 530/328; 530/350
(58) Field of Search ............................... 514/2, 12, 15, 514/21; 530/300, 328, 350

(56) References Cited

U.S. PATENT DOCUMENTS 5,710,132 A    1/1998   Moller et al.

FOREIGN PATENT DOCUMENTS

| DE | 9743905 | 11/1997 |
|----|---------|---------|
| GB | 2289278 | 11/1995 |
| GB | 9814473 | 4/1998 |
| HU | 208089 B | 4/1989 |
| WO | 9705884 | 2/1997 |

OTHER PUBLICATIONS

Kruzel, Journal of Molecular Neuroscience, 2001, 17, pp. 379–389.*
Inglot, Archivum Immunologiae et Therapiae Experimentalis, 1996, 44, pp. 215–224.*
Janusz, Archivum Immunologiae et Therapiae Experimentalis, 1993, 41, pp. 275–279.*
Inglot et al., Archivum Immun. et Ther. Exper., vol. 44, 1996, pp. 215–224.*
Burrin, "Nutrient–independent and nutrient–dependent factors stimulate protein synthesis in colostrum–fed newborn pigs" 1995, Pediatric Research, vol. 37, pp–593–599.*
Staroscik et al, Molecular Immunology, vol. 30, No. 12, pp. 1277–1282, 1983.*
Haraba et al, Arch. Immun. Ther. Exp. 1986, pp. 437–443.*
Zimecki, Arch. Immun Ther. Exp. 1991, pp. 461–467.*
Janusz et al., Arch. Immun. Ther. Exp., 1993, pp. 175–279.*
Janusz et al., Isolation And Characterization Of A Poline–Rich Polypeptide From Ovine Colostrum, FEBS Letters, vol. 49, No. 2, Dec. 1974, pp. 276–279.
Janusz et al., "Chemical and physical characterization of a proline–rich polypeptide from sheep colostrum," The Biochemical Journal, vol. 1999, pp. 9–15, 1981.
Starościk et al., "Immunologically Active Nonpeptide Fragment Of A Proline–Rich Polypeptide From Ovine Colostrum: Amino Acid Sequence And Immunoregulatory Properties," Molecular Immunology, vol. 30., No. 12, pp. 1277–1282, 1983.
Japanese Patent Abstract, Application No. 01085119, Publication No. 02265458, Publication Date Oct. 30, 1990.
Hraba et al., "Effect of Proline–Rich Polypeptide on Experimental Autoimmune Response to Erythrocytes," Archivum Immunolgiae et Therapiae Experimentalis, 1986, pp. 437–443.
Zimecki et al., "Effect of a Proline–Rich Polypeptide (PRP) on the Development of Hemolytic Anemia and Survival of New Zealand Black (NZB) Mice," Archivum Immunologiae et Therapiae Experimentalis, 1991, pp. 461–467.
Unlisted Drugs, Mar. 1989, vol. 41, No. 3, p. 52.
Janusz et al., "Proline–Rich Polypeptide (PRP)—an Immunomodulatory Peptide from Ovine Colostrum," Archivum Immunologiae et Therapiae Experimentalis, 1993, pp. 175–279.
Inglot et al., "Colostrinine: a Proline–Rich Polypeptide from Oviine Colostrum Is a Modest Cytokine Inducer in Human Leukocytes," Archivum Immunologiae et Therapiae Experimentalis, 1996, pp. 215–223.
Abstract entitled "Colostrinin For Treatment Of Alzheimer's Disease," European Cytokine Network vol. 7, No. 3—Estimated Publication Oct. 4, 1996.

* cited by examiner

Primary Examiner—Christopher Tate
Assistant Examiner—Roy Teller
(74) Attorney, Agent, or Firm—Rankin, Hill, Porter & Clark LLP

(57) ABSTRACT

The use of Colostrinin as a medicament, particularly in the treatment of chronic disorders of the central nervous system and the immune system.

32 Claims, No Drawings

SEQUENCE LISTING

<160> NUMBER OF SEQ ID NOS: 1

<210> SEQ ID NO 1
<211> LENGTH: 9
<212> TYPE: PRT
<213> ORGANISM: Ovis aries

<400> SEQUENCE: 1

Val Glu Ser Tyr Val Pro Leu Phe Pro
1               5

COLOSTRININ, AND USES THEREOF

This application is the U.S. National Phase of PCT/GB97/02721 filed Oct. 3, 1997.

The present invention relates to Colostrinin, and to its use as a medicament.

Colostrum is the thick, yellowish fluid produced by a mammalian mother's breasts during the first few days after childbirth. It is replaced by mature breast milk about four to five days after birth. Compared with mature breast milk, colostrum contains low sugar. However, colostrum is richer in lipids, protein, mineral salts, vitamins and immunoglobulin. It also contains various floating cells such as granular and stromal cells, neutrophils, monocyte/macrophages and lymphocytes and includes growth factors, hormones and cytokines.

Various factors have been isolated and characterised from mammalian colostrum. In 1974, Janusz et al (FEBS Lett., 49, 276–279) isolated a proline-rich polypeptide (PRP) from ovine colostrum. The contents of this reference are incorporated herein by reference. It has since been discovered that mammals other than sheep have analogues of PRP as a component of their colostrum. PRP has since been called Colostrinin and is tentatively identified as a new class of cytokine.

Janusz et al in "Proline-Rich Polypeptide (PRP)—an Immunomodulatory Peptide from Ovine Colostrum" (Archivum Immunologiae et Therapiae Experimentalis, 1993, 41, 275–279) mentioned that PRP from ovine colostrum has immunotropic activity in mice. However, there was no suggestion in this document that the PRP would have any therapeutic effect on any other animal. It will be appreciated that the fact that a composition has a therapeutic effect on mice cannot be taken to suggest that there will be a therapeutic effect on any other animal.

We have now found that Colostrinin has a number of previously unknown therapeutic effects. More particularly, we have found that Colostrinin provides an immunotropic action and provides a psychotropic action.

According to one aspect of the invention we provide Colostrinin for use as a medicament. The Colostrinin may be used as a medicament for non-rodent mammals; we have found that Colostrinin is especially useful as a medicament for the treatment of humans.

According to another aspect of the invention there is provided the use of Colostrinin in the manufacture of a medicament for treating disorders of the central nervous system or disorders of the immune system.

In one advantageous embodiment of the invention, the Colostrinin is for use in the treatment of disorders of the central nervous system, particularly chronic disorders of the central nervous system. The disorders of the central nervous system that may be treated with Colostrinin include neurological disorders and mental disorders.

Examples of neurological disorders that can, with advantage, be treated by Colostrinin include dementia, and also disorders that cause dementia, such as neurodegenerative disorders. Neurodegenerative disorders include, for example, senile dementia and motor neurone disease; Parkinson's disease is an example of a motor neurone disease that can be treated with Colostrinin. Colostrinin has been found particularly effective in the treatment of the neurodegenerative disease known as Alzheimer's disease.

Examples of mental disorders that can, with advantage, be treated by Colostrinin include psychosis and neurosis. For example, the Colostrinin may be used to treat emotional disturbances, especially the emotional disturbances of psychiatric patients in a state of depression—the use of Colostrinin has been found to help the patient with an improvement in feelings of wellbeing and with mood stabilisation. The Colostrinin may also be used as an auxiliary withdrawal treatment for drug addicts, after a period of detoxification, and in persons dependent on stimulants.

In another advantageous embodiment of the invention, the Colostrinin is for use in the treatment of disorders of the immune system, particularly chronic disorders of the immune system. Thus, we have found that Colostrinin can be used in the treatment of disease requiring immunomodulation. In particular, we have found that Colostrinin is useful for treating such disorders in non-rodent animals, including humans. Colostrinin is useful in the treatment of a variety of diseases with an immunological and infectious basis. For example, the Colostrinin can be used to treat chronic diseases with a bacterial and viral aetiology, and to treat acquired immunological deficiencies that have developed, for example, after chemotherapy or radiotherapy of neoplasms. The invention is particularly useful for treating chronic bacterial and viral infections requiring non-specific immunostimulation and immunocorrection.

In general, a chronic disorder is a disorder that has persisted for a long time, usually at least one week, more usually at least one month, and often at least 3 months or at least 6 months.

It is a feature of the present invention to use Colostrinin for improving the development of the immune system of a new born child. It is a further feature of the invention to use Colostrinin to correct immunological deficiencies in a child. These uses of the Colostrinin may be particularly applicable to babies or children who have been deprived of colostrum. This may occur, for example, in babies and children who were not breast fed from birth; the artificial feed that such babies and children would have been given does not contain Colostrinin.

According to another aspect of the invention, we provide the use of Colostrinin as a dietary supplement. Colostrinin is particularly advantageously used as a dietary supplement for babies and young children to correct deficiencies in the development of their immune system. As noted above, such deficiencies would arise in babies and children who had not been breast fed from birth. The Colostrinin may also be used as a dietary supplement for adults who have been subjected to chemotherapy, or have suffered from cahexia, or weight loss due to chronic disease. In an aspect of the invention, we provide a dietary supplement comprising an orally ingestible combination of Colostrinin in combination with a physiologically acceptable carrier. The dietary supplement may be provided in liquid or solid form; the dietary supplement may suitably be provided in the form of a tablet.

In accordance with the invention, the Colostrinin may be administered prophylactically in order to help to prevent the development of disorders of the central nervous system and the immune system.

The Colostrinin used in the aspects of the invention described above may be ovine Colostrinin, or it may be non-ovine Colostrinin. Non-ovine Colostrinin may be derived from the colostrum of, for example, humans, cows, horses, goats, pigs, yaks, llamas and asses. The colostrum will normally be present in the beestings of these animals for 1 to 4 days after parturition.

The term "Colostrinin", as used herein refers to a polypeptide which, in its natural form, is obtained from mammalian colostrum. Colostrinin is sometimes known as "colostrinine", and has the following properties:

(i) it has a molecular weight in the range 16,000 to 26,000 Daltons;

(ii) it is a dimer or trimer of sub-units each sub-unit having a molecular weight in the range 5,000 to 10,000 Daltons, preferably 6,000 Daltons;

(iii) it contains proline, and the amount of proline is greater than the amount of any other single amino acid.

We have also found that the Colostrinin, and also the sub-units making up the Colostrinin, are non-polar.

The molecular weight can be determined by electrophoresis in the presence of SDS; the presence of the dimer or trimer can be shown by the same technique. It can be shown that the bonds between the sub-units are non-covalent by electrophoresis in reduced and non-reduced conditions. The presence of proline can be established by conventional amino acid analysis. The non-polarity can be demonstrated by chromatography in non-polar conditions.

The Colostrinin used in the present invention may be ovine-Colostrinin or non-ovine Colostrinin. Ovine Colostrinin has a molecular weight of about 18,000 Daltons, is made up of three non-covalently linked sub-units each having a molecular weight of about 6,000 Daltons and includes about 22 wt % proline. The amino-acid composition is made up of the following number of residues per sub-unit: lysine-2, histidine-1, arginine-0, aspartic acid-2, threonine-4, serine-3, glutamic acid-6, proline-11, glycine-2, alanine-0, valine-5, methionine-2, isoleucine-2, leucine-6, tyrosine-1, phenylalanine-3 and cysteine-0.

As noted above, in its natural form Colostrinin is derived from mammalian colostrum. Colostrinin can be derived from mammalian colostrum by removing the lipids and the majority of the proteins from the colostrum. Broadly, Colostrinin can be obtained from the beestings of, for example, large farm animals using column chromatography techniques and other biochemical techniques, or can be obtained by genetic engineering techniques.

More particularly, Colostrinin may be isolated from mammalian colostrum by using the following steps:

(i) Removing lipids, for example by centrifugation;

(ii) Removing proteins such as casein, for example, by lowering pH;

(iii) separating Colostrinin bound to immunoglobulin, for example by:
  (a) Processing the whey formed after the removal of lipids and proteins by ion exchange chromatography; and
  (b) Eluting with phosphate buffered saline and collecting a fraction containing Colostrinin bound to immunoglobulin, for example IgG2 in sheep;

(iv) Separating Colostrinin from the immunoglobulin, for example by sieving chromatography; and (v) Further purifying the Colostrinin, preferably by:
  (a) De-salting the fraction below 30,000 Daltons molecular weight; and
  (b) Introducing antibodies to immunoglobulins and thereby remove this class of proteins to obtain the final product.

Whilst the above definition relates to naturally occurring mammalian Colostrinin, the term Colostrinin as herein used also includes analogues and fragments thereof having substantially the same biological activity, and mammalian Colostrinin, analogues thereof and fragments thereof produced by recombinant DNA technology. Colostrinin as used herein also includes biologically active polypeptides of substantially the same composition as natural Colostrinin, which have been made by polypeptide synthesis.

In a further aspect of the present invention there is provided a method of treating disorders of the central nervous system or of the immune system using Colostrinin. The disorders that can, with advantage, be treated using the method according to the invention are described above. In a preferred embodiment the Colostrinin is administered to a patient for a first period at about 1 to 2 therapeutic units daily, followed by a second period when no Colostrinin is administered. The first period is preferably about 2 to 4 weeks, more preferably about 3 weeks; and the second period is preferably about 2 to 5 weeks, more preferably about 4 weeks. This cycle is preferably repeated at least once, and is more preferably repeated more than once.

The therapeutic unit for use in methods of the invention is preferably in the range 25 to 1,000 micrograms of Colostrinin, most preferably 50 to 100 micrograms.

The Colostrinin may be formulated for administration in any suitable form. For example, is may be formulated for oral, rectal or parenteral administration. More specifically, the Colostrinin may be formulated for administration by injection, or, preferably, in a form suitable for absorption through the mucosa of the oral/nasopharyngeal cavity, from the alimentary canal or any other mucosal surface. The oral formulations may be provided in a form for swallowing; or, preferably, in a form for dissolving in the saliva, whereby the formulation can be absorbed in the mucous membranes of the oral/nasopharyngeal cavity. The oral formulations may be in the form of a tablet for oral administration, lozenges (i.e. a sweet-like tablet in a form suitable to be retained in the mouth and sucked), adhesive gels for rubbing into the gum. The Colostrinin may be formulated as an adhesive plaster or patch, which may be applied to the gums. The Colostrinin may also be formulated for application to mucous-membranes of the genito-urinary organs.

Whilst it would, of course, be possible to administer the Colostrinin in the form of whole colostrum, this is not preferred, because whole colostrum has an unpleasant taste, and is difficult to store.

Colostrinin for use in the present invention may be obtained from any mammal, including human sources or animals such as cows, horses, goats, pigs, yaks, sheep, llamas or asses, camels etc.

Tests on Colostrinin were performed using ovine and human Colostrinin. Ovine Colostrinin is marketed under the trade mark Colostrinin™.

During tests on experimental animals it was found that Colostrinin is characterized by immunotropic action, both in vivo and in vitro, based on the properties of modulation, development of differentiation and maturation, of thymocytes to active T cells and on the stimulation or inhibition of an immunological response, and on induction of the expression of various surface markers on the thymocytes. In intraperitoneal administration in mice, Colostrinin inhibits the development of haemolytic anaemia in mice of the NZB line, inhibit the growth of sarcoma 180 in mice, and in mice exposed to gamma radiation it protects the animals against radiation sickness. Toxicological studies on mice showed, both after oral and parenteral administration, a very low toxicity, as LD50 is above 1.25 g/kg of body weight. Colostrinin also exhibits capacity to stimulate the growth, maturation and differentiation of immunologically active cells both in humans and in experimental animals. In cultures of lymphocytes of human peripheral blood (including cultures of lymphocytes isolated from the cord blood) Colostrinin is characterized in that it stimulates the production of cytokines, especially gamma interferon (IFN-γ), tumour necrosis factor (TNF-α), interleukins (e.g. IL-6 and IL-10) and various growth factors. The cytokines produced are determined quantitatively by known methods.

In natural conditions analogues of ovine Colostrinin but possessing the biochemical properties thereof are present in human colostrum and in the beestings of all mammals, and especially large farm animals such as cows, horses, goats, pigs, yaks, sheep, llamas or asses, camels etc. for 1–4 days after parturition. The Colostrinin enters the body of the newborn animals during sucking and swallowing of its mother's colostrum. Owing to the low molecular weight it is possible for Colostrinin to act on the mucosa of the oral/nasopharyngeal cavity via cell receptors, and even as a result of ordinary diffusion. Because the mucosa and epithelium of the upper part of the digestive tract contain receptors for certain immunomodulators, it has been shown in investigations that the Colostrinin can be administered in the form of tablets and sublingual tablets for sucking, tablets and capsules for swallowing, in the form of adhesive gels, and in the form of adhesive plasters for fastening to the gums. Colostrinin can also be applied to the mucous membranes of genito-urinary organs.

Scientific studies aiming to elucidate the biochemical activity induced by Colostrinin also revealed the existence of similar biological activity when using human colostrum, collected from women in the period of 1–7 days after parturition. The method used for isolating Colostrinin of human origin was analogous to the methods of obtaining it from the beestings of farm animals, and especially from sheep beestings. It was found that the colostrum secreted by the mammary gland of women from 1–7 days after parturition contains the polypeptide Colostrinin, the amount of which depends on lactation and is optimum between 2–3 days, when about 300 mg of it is detected in 1 liter of colostrum. This quantity of human Colostrinin is within the range seen in ovine colostrum. It was demonstrated that human Colostrinin has many biological properties similar to, for example, the sheep analogue. It was found that Colostrinin originating from human colostrum stimulates the lymphocytes present in the colostrum, and cord blood lymphocytes, to secrete cytokines, including mainly interferon (IFN-γ), turnout necrosis factor TNF-α, interleukins (IL-10 and IL-6) and other cytokines. These cytokines are involved in humoral and cellular immune reactions.

These biological activities of the Colostrinin both of human and of animal origin were determined by the method known from a Polish patent (PL 170592 B1) and from European patent no. EP-B-0609225, pt.: Testing Immunology.

In studies on human volunteers it was shown that after administration of tablets for sucking, containing at least 25 μg of Colostrinin at doses of at least one daily, for a period of about 3 weeks, no adverse reactions were observed; on the other hand it brings about a state of hyporeactivity to induction of interferon IFN-γ and partially also of tumour necrosis factor TNF-α. After discontinuing administration of the Colostrinin, the state of hyporeactivity returns to normal. The reactions obtained are the result of involvement of cytokines produced by Th1 and Th2 lymphocytes and by helper cells.

During clinical studies it was shown in addition that Colostrinin has an immunomodulatory effect and an effect on the central nervous system, which can be utilized prophylactically and therapeutically in the following diseases, e.g. for preventing occurrence of, progression of and for remission of Alzheimer's disease, in senile dementia of some other origin and in the treatment of chronic diseases with an immunologic and infectious basis.

Instead of Colostrinin, it is possible to use a nonapeptide designated NP having the following composition and amino acid sequence: Val-Glu-Ser-Tyr-Val-Pro-Leu-Phe-Pro. (SEQ ID NO:1) NP can be obtained from Colostrinin by digesting with chymotrypsin and isolation by column chromatography, or by means of chemical synthesis. NP is an example of a useful fragment of Colostrinin. It has been found to have similar biological effects to Colostrinin, and, in particular, is useful for treating the chronic immune and central nervous system disorders described above, especially Alzheimer's disease. NP may be used to treat any of disorders described above. It may also be used in a dietary supplement. It may be formulated in the same way as Colostrinin. NP is useful for the treatment of mammals, especially humans.

In order that the invention may be more fully understood, reference will now be made to the accompanying Examples by way of illustration only.

EXAMPLE I

In ovine Colostrinin with molecular weight of 18 000 Daltons, constructed from three non-covalently linked sub-units with molecular weight of 6 000 Daltons, each sub-unit had the following amino-acid composition:

| Amino Acid | No. of residues per subunit |
|---|---|
| Lysine | 2 |
| Histidine | 1 |
| Arginine | 0 |
| Aspartic Acid | 2 |
| Threonine | 4 |
| Serine | 3 |
| Glutamic acid | 6 |
| Proline | 11 |
| Glycine | 2 |
| Alanine | 0 |
| Valine | 5 |
| Methionine | 2 |
| Isoleucine | 2 |
| Leucine | 6 |
| Tyrosine | 1 |
| Phenylalanine | 3 |
| Cysteine | 0 |

The Colostrinin was obtained from sheep beestings, taken after parturition up to 24 hours after commencement of lactation. The material was centrifuged at 35 000×g in order to remove fats and part of the casein. The Ig fraction obtained was applied to a DEAE-Cellulose column, in order to isolate immunoglobulin IgG2 complexed with the polypeptide Colostrinin, and upon elution from the column the Colostrinin was separated from the IgG2 by means of column chromatography on Sephadex G-100 and was chromatographed again on Sephadex G-75. Then a fraction of this polypeptide was applied to a column of Sepharose conjugated with anti-bodies against sheep IgG2 to remove traces of IgG2 contamination. The preparation obtained was desalinated by means of Sephadex G-25 and lyophilized, after which it was stored at a temperature of +4° C. or −20° C.

The Colostrinin thus obtained has been designated by the trade mark Colostrinin™.

In polyacrylamide gel electrophoresis in the presence of SDS, a strong band was observed, corresponding to molecular weight of 5 800 Daltons, and two weak bands corresponding to molecular weight of 12 400 Daltons and 18 200 Daltons;

EXAMPLE II

The nonapeptide NP having the composition and amino acid sequence Val-Glu-Ser-Tyr-Val-Pro-Leu-Phe-Pro (SEQ ID NO:1) was obtained from the Colostrinin made in Example I.

50 mg of the Colostrinin is digested by means of 10 activity units of the proteolytic enzyme chymotrypsin, for 20 hours at a temperature of 30° C. Isolation from the product of digestion was carried out by means of at least one cycle of column chromatography using Sephadex G-10. The preparation obtained was lyophilised, and was then stored at a temperature of +4° C. or −20° C. The isolated nonapeptide was isolated by means of determination of the N-terminal amino acid.

EXAMPLE III

Dosage unit in the form of a tablet for sucking, with the composition:

| | | |
|---|---|---|
| Active ingredient: | Colostrinin ® polypeptide obtained according to Example I | 0.0001 g |
| Stabilizer: | Albumin, free from impurities, mainly I.P.S. | 0.000135 g |
| Lubricant/binder: | Magnesium stearate | 0.003 g |
| Carrier: | Mannitol | 0.15 g (0.1497 g) |

The above components were suspended in 0.0001 M NaCl. Tablets for sucking are primarily intended for treating early and late stages of dementia, including Alzheimer's disease, and various stages of senile dementia, for treating chronic bacterial and viral infections, requiring non-specific immunostimulation and immunocorrection and acquired immunologic deficiencies caused by various agents. In addition it is used in emotional disturbances especially in states of depression in psychiatric patients to improve the general feeling of well being and for mood stabilization, and in auxiliary withdrawal treatment of drug addicts, after a period of detoxification and in persons dependent on stimulants. Colostrinin™ can also be used in the newborn and in young children for correcting nutritional deficiencies connected with artificial feeding.

EXAMPLE IV

Preparation in the form of gel for application to mucous membranes with the composition:

| | |
|---|---|
| Active ingredient: | Colostrinin ™ polypeptide obtained according to Example I |
| Stabilizer | Albumin |
| Gel carrier: | Orabase-Plain ® containing pectin, gelatin, sodium salt of carboxymethylcellulose and hydrocarbon gel |

0.0003 g of the polypeptide Colostrinin™ and 0.0015 g of albumin were used per 1 ml of gel carrier. The dosage unit thus formulated is primarily intended for cyclic treatment of bacterial and viral infections of the oral cavity and upper respiratory tract.

EXAMPLE V

Preparation in the form of intramuscular, subcutaneous or intravenous injections.

| | |
|---|---|
| Active ingredient: | Colostrinin ™ polypeptide obtained according to Example I |
| Stabilizer: | Human albumin, free from impurities |
| Carrier: | Sterile, none pyrogenic water |

0.0003 g of Colostrinin™ polypeptide, 0.0015 g of albumin and, as antibacterial agent, 0.001% of Merthiolate, i.e. sodium salt of ethylmercurithiosalicylic acid, were used per 1 ml ampoule. The dosage unit thus obtained is primarily intended for cyclic treatment of bacterial and viral infections.

EXAMPLE VI

Preparation in the form of intramuscular, subcutaneous or intravenous injections.

| | |
|---|---|
| Active ingredient: | NP obtained according to Example II |
| Stabilizer: | Human albumin, free from impurities |
| Carrier: | Sterile, none pyrogenic water |

0.0003 g of NP, 0.0015 g of albumin and, as antibacterial agent, 0.0010% of Merthiolate, i.e. sodium salt of ethylmercurithiosalicylic acid, were used per 1 ml ampoule. The dosage unit thus obtained is primarily intended for cyclic treatment of bacterial and viral infections.

EXAMPLE VII

Induction of cytokines by the polypeptide Colostrinin™ in vitro on blood taken from healthy and sick volunteers taking the pharmaceutical in the form stated in Example III, in cyclic treatment, is carried out as follows.

Whole blood, containing 10 units per 1 ml of heparin without preservatives is diluted at 1:10 ratio in RPMI 1640 culture medium. Incubation is conducted in the same culture medium without inducers (negative control), or in the presence of 1–100 $\mu$g/ml of the polypeptide Colostrinin™ or in the presence of 2 $\mu$g/ml blood of phytohaemagglutinin (PHA) and 2 $\mu$g/ml blood of lipopolysaccharide (LPS), at a temperature of 37° C., in an atmosphere of 5% carbon dioxide, for 20 hours. Samples with mixture of PHA and LPS are the positive control, as they can stimulate the maximum quantities of cytokines. The test results are presented in the Tables 1 and 2. They show that Colostrinin™ at concentrations of 1–100 $\mu$g/ml stimulates the production of cytokines in a dose-dependent fashion. Relative to the negative control (without inducers) these results are statistically significant ($p<0.0001$). Patients with Alzheimer's disease exhibit diminished capacity for production of IFN and to a lesser extent also TNF.

TABLE 1

Induction of cytokines by Colostrinin ™ (series A 1993) from sheep in cultures of lymphocytes present in whole blood of healthy volunteers or of patients with Alzheimer's disease.

| Blood donors | Inducers | Dose ($\mu$g/ml) | Cytokines (unit/ml ± SD) | |
|---|---|---|---|---|
| | | | IFN | TNF |
| Healthy volunteers | Colostrinin ™ | 100 | 344 ± 254 | 670 ± 560 |
| | Colostrinin ™ | 10 | 50 ± 59 | 316 ± 371 |
| | PHA + LPS | 2 + 2 | 171 ± 162 | 521 ± 447 |
| | Control | — | 9 ± 21 | 19 ± 26 |
| Patients with Alzheimer's disease | Colostrinin ™ | 100 | 21 ± 14 | 249 ± 187 |
| | Colostrinin ™ | 10 | 15 ± 9 | 182 ± 158 |
| | PHA + LPS | 2 + 2 | 117 ± 76 | 397 ± 252 |
| | Control | — | 2 ± 3 | 18 ± 26 |

The group of healthy volunteers (22 people) was heterogeneous (age range 20–64 years). The group of patients with Alzheimer's disease (50 people) was also heterogeneous (age 63±7.5 years). Despite the high standard deviation (±SD) the differences between the controls without inducers (absent) and Colostrinin™ were statistically significant ($p<0.001$).

TABLE 2

Examples of stimulation of the production of interferon (IFN) by Colostrinin ™ (series A 1993) from sheep in experiments using whole blood of healthy volunteers and patients with various diseases.

| Blood donors (diagnosis) | Inducer | Dose ($\mu$g/ml) | Titres of IFN determined by | |
|---|---|---|---|---|
| | | | Antivirus biotest units/ml | ELISA IFN-$\gamma$ pg/ml |
| Z. B. healthy young soldier | Colostrinin ™ | 100 | 300 | 2920 |
| | Colostrinin ™ | 10 | 300 | 3402 |
| | Colostrinin ™ | 1 | 100 | 1413 |
| | PHA + LPS | 2 + 2 | 200 | 3308 |
| | Control | — | <3 | 24 |
| C. D. healthy young soldier | Colostrinin ™ | 100 | 600 | 3941 |
| | Colostrinin ™ | 10 | 200 | 3778 |
| | Colostrinin ™ | 1 | 100 | 2690 |
| | PHA + LPS | 2 + 2 | 600 | 4631 |
| | Control | — | 5 | 55 |
| M. J. Alzheimer's disease | Colostrinin ™ | 100 | 40 | 400 |
| | Colostrinin ™ | 10 | 20 | 427 |
| | PHA + LPS | 2 + 2 | 300 | 3757 |
| | Control | — | 3 | 46 |
| S. E. schizophrenia | Colostrinin ™ | 100 | 6 | 29 |
| | Colostrinin ™ | 10 | 6 | 29 |
| | PHA + LPS | 2 + 2 | 30 | 243 |
| | Control | — | 3 | 19 |
| F. W. breast cancer | Colostrinin ™ | 100 | 70 | 523 |
| | Colostrinin ™ | 10 | 50 | 307 |
| | PHA + LPS | 2 + 2 | 600 | 2833 |
| | Control | — | 40 | 150 |

NOTE: the biotest for presence of IFN measures the levels of various types of interferons, whereas the ELISA test only determines the level of immunoactive IFN-$\gamma$.

EXAMPLE VIII

Cord blood obtained from the Gynaecological-Obstetric Department of the Specialist District Hospital in Wroclaw. Induction of cytokines by Colostrinin™ in vitro in lymphocytes of cord blood taken 4–6 hours after parturition is effected in the following way.

The lymphocytes are isolated using a Ficoll-Paque® gradient containing 5.7 g of the component Ficoll 400 and 9.0 g of the component Diatrizoate Sodium per 100 ml. The lymphocytes isolated are suspended in RPMI-1640 culture medium at density of $2 \times 10^6$ lymphocyte cells per 1 ml of culture medium. Colostrinin™ at concentration of 1–20 $\mu$g/ml or phytohaemagglutinin at concentration of 10 $\mu$g/ml is added to the lymphocyte suspension. The culture is incubated for 20 hours at a temperature of 37° C. Then the level of cytokines in the culture fluids is determined by biological methods. A typical example is given in Table 3. Colostrinin™ at concentration of 1–100 $\mu$g/ml has capacity for stimulation of cytokines (IFN and TNF) similar to that exhibited by the classical IFN-$\gamma$ inducer-phytohaemagglutinin.

TABLE 3

Induction of cytokines by Colostrinin ™ (series A 1996) in a culture of lymphocytes isolated from cord blood (CBL).

| N | Inducer | Dose ($\mu$g/ml) | Cytokines (unit/ml ± SD) | |
|---|---|---|---|---|
| | | | IFN | TNF |
| 32 | Colostrinin ™ | 20 | 89 ± 79 | 59 ± 41 |
| 39 | Colostrinin ™ | 10 | 78 ± 80 | 37 ± 35 |
| 17 | Colostrinin ™ | 1 | 38 ± 66 | 16 ± 17 |
| 50 | PHA | 10 | 75 ± 66 | 83 ± 69 |
| 50 | control | — | 3 ± 3 | 3 ± 4 |

N - number of CBL samples investigated
In the Student t test the probability (p) of significance of the difference Colostrinin ™
— "absent", both for IFN and TNF, is $p < 0.0001$.

Because the cord blood is rich in immature stem cells, which are capable of reproduction of haemopoietic cells and of various immunologically-active cells, the result obtained shows that Colostrinin™ greatly accelerates the maturation of stem cells. The results obtained show that it is possible to use Colostrinin™ for treating various types of immune defiencies and for stimulating the haemopoietic system, e.g. after injuries, infections, chemotherapy and radiotherapy. In biomedical studies, substances of natural origin with similar action are very seldom encountered.

EXAMPLE IX

The method of treatment of disorders of the central nervous system was investigated on a group of volunteer patients in the early and moderate stages of Alzheimer's disease. The dosage units were administered in the form of tablets for sucking, between meals, containing 0.00015 g of Colostrinin™ defined in Examples I and III. Firstly, 1 tablet was used daily for a period of 3 weeks, then therapy was interrupted for 2–4 weeks and treatment was repeated, administering 2 tablets daily for 3 weeks. It was found that Colostrinin™ treatment induced a state of hyporeactivity or tolerance. This is manifested by an inability to synthesise IFN and also tumour necrosis factor TNF-$\alpha$. This phenomenon permits quantitative measurements of the action of active agent.

After cessation of administration of these drugs the state of tolerance reverses spontaneously. The state of temporary tolerance to the Colostrinin™ is a result of the involvement of cytokines produced by Th1 and Th2 lymphocytes and helper cells such as monocytes, macrophages, dendritic cells, and endothelial cells and their products. As a result, improvement of contact and uplift of mood were observed in patients with Alzheimer's disease.

FIG. 1 illustrates the appearance and spontaneous disappearance of a state of hyporeactivity (partial tolerance) to induction of gamma interferon (IFN-$\gamma$) in a female patient (J.M.) with Alzheimer's disease, who received Colostrinin™ in 100-µg tablets every other day for three weeks. This was followed by a 3-week pause in treatment (during the pause, the tolerance to the inducer returns to normal). Blood samples for investigating stimulation of IFN-γ by Colostrinin™ and control inducers (PHA-10 µg/ml) were taken every week. The method of performing the tests for induction of cytokines and their quantitative determination were described in previous sections.

The results of determinations of levels of induced IFN-γ showed that hyporeactivity appears as early as during the first week of taking Colostrinin™ (100 µg/tablet every other day) and is maximum in the third week of treatment. Reversal of the state of tolerance to induction of IFN-γ occurred spontaneously in a period of 3 weeks of a pause in treatment (i.e. in the sixth week after commencement of treatment). Moreover, this chart shows that hyporeactivity that is "specific" with respect to sheep Colostrinin™ (OvCal) is still maintained in the sixth week of observation, whereas hyporeactivity to PHA had disappeared completely.

EXAMPLE X

The method of treatment of disorders of the central nervous system was investigated on a group of volunteer patients in the early stages of Alzheimer's disease. The dosage units were administered in the form of tablets for sucking between meals, containing 0.00015 g of NP defined in Example II. Firstly, 1 tablet was used daily for a period of 3 weeks, then therapy was interrupted for 3 weeks and treatment was repeated, administering 2 tablets daily for 3 weeks. It was found that NP treatment induced a state of hyporeactivity or tolerance. This is manifested by an inability to synthesise IFN and also tumour necrosis factor TNF-α. This phenomenon permits quantitative measurements of the action of active agent.

After cessation of administration of these drugs the state of tolerance reverses spontaneously. The state of temporary tolerance to the NP is a result of the involvement of cytokines produced by Th1 and Th2 lymphocytes and helper cells such as monocytes, macrophages, dendritic cells, and endothelial cells and their products. As a result, improvement of contact and uplift of mood were observed in patients with Alzheimer's disease.

3. The method according to claim 1, wherein the therapeutic unit of Colostrinin is in the range of about 25 to 1000 micrograms.

4. The method according to claim 1 wherein the therapeutic unit of Colostrinin in isolated form is administered to the patient about one or two times each day for a first period of time, followed by a second period of time when no Colostrinin is administered.

5. The method according to claim 4 wherein the first period of time is in the range of about 2 to 4 weeks, and the second period of time is in the range of about 2 to 5 weeks.

6. The method according to claim 4 wherein a cycle of administering Colostrinin in isolated form for a first period of time followed by a second period of time when Colostrinin is administered is repeated at least once.

7. A method of treating a human patient afflicted with Alzheimer's Disease comprising administering a composition comprising a therapeutic unit of Colostrinin in isolated form to the human patient about one or two times per day for a predetermined period of time.

8. The method according to claim 7, wherein the Colostrinin is non-ovine Colostrinin.

9. The method according to claim 7, wherein the therapeutic unit of Colostrinin is in the range of about 25 to 1000 micrograms.

10. The method according to claim 7 wherein the therapeutic unit of Colostrinin in isolated form is administered to the patient about one or two times each day for a first period of time, followed by a second period of time when no Colostrinin is administered.

11. The method according to claim 10 wherein the first period of time is in the range of about 2 to 4 weeks, and the second period of time is in the range of about 2 to 5 weeks.

12. The method according to claim 10 wherein a cycle of administering Colostrinin in isolated form for a first period of time followed by a second period of time when Colostrinin is administered is repeated at least once.

13. A method of treating a human patient afflicted with dementia comprising administering up to two therapeutic units of Colostrinin in isolated form to the human patient per day, wherein each therapeutic unit of Colostrinin is in the range of about 25 to 1000 micrograms.

14. The method according to claim 13 wherein the up to two therapeutic units of Colostrinin in isolated form are

What is claimed is:

1. A method of treating a human patient afflicted with dementia comprising administering a composition comprising a therapeutic unit of Colostrinin in isolated form to the human patient about one or two times per day for a predetermined period of time.

2. The method according to claim 1 wherein the Colostrinin is non-ovine Colostrinin.

administered to the patient every day or every other day for a first period of time followed by a second period of time when no therapeutic units of Colostrinin are administered to the human patient.

15. The method according to claim 14 wherein the first period of time is in the range of about 2 to 4 weeks, and the second period of time is in the range of about 2 to 5 weeks.

16. The method according to claim 15 wherein a cycle of administering Colostrinin in isolated form for the first period of time followed by the second period of time when Colostrinin is administered is repeated at least once.

17. The method according to claim 13 wherein the Colostrinin is formulated for oral administration.

18. A method of treating a human patient afflicted with Alzheimer's Disease comprising administering up to two therapeutic units of Colostrinin in isolated form to the human patient per day, wherein each therapeutic unit of Colostrinin is in the range of about 25 to 1000 micrograms.

19. The method according to claim 18 wherein the up to two therapeutic units of Colostrinin in isolated form are administered to the patient every day or every other day for a first period of time followed by a second period of time when no therapeutic units of Colostrinin are administered to the human patient.

20. The method according to claim 19 wherein the first period of time is in the range of about 2 to 4 weeks, and the second period of time is in the range of about 2 to 5 weeks.

21. The method according to claim 20 wherein a cycle of administering Colostrinin in isolated form for the first period of time followed by the second period of time when Colostrinin is administered is repeated at least once.

22. The method according to claim 18 wherein the Colostrinin is formulated for oral administration.

23. A method of treating a human patient afflicted with dementia comprising administering up to two therapeutic units of a nonapeptide having the amino acid sequence Val-Glu-Ser-Tyr-Val-Pro-Leu-Phe-Pro (SEQ ID NO: 1) in isolated form to the human patient per day, wherein each therapeutic unit of the nonapeptide is in the range of about 25 to 1000 micrograms.

24. The method according to claim 23 wherein the up to two therapeutic units of the nonapeptide in isolated form are administered to the patient every day or every other day for a first period of time followed by a second period of time when no therapeutic units of the nonapeptide are administered to the human patient.

25. The method according to claim 24 wherein the first period of time is in the range of about 2 to 4 weeks, and the second period of time is in the range of about 2 to 5 weeks.

26. The method according to claim 25 wherein a cycle of administering the nonapeptide in isolated form for the first period of time followed by the second period of time when the nonapeptide is administered is repeated at least once.

27. The method according to claim 23 wherein the nonapeptide is formulated for oral administration.

28. A method of treating a human patient afflicted with Alzheimer's Disease comprising administering up to two therapeutic units of a nonapeptide having the amino acid sequence Val-Glu-Ser-Tyr-Val-Pro-Leu-Phe-Pro (SEQ ID NO: 1) in isolated form to the human patient per day, wherein each therapeutic unit of the nonapeptide is in the range of about 25 to 1000 micrograms.

29. The method according to claim 28 wherein the up to two therapeutic units of the nonapeptide in isolated form are administered to the patient every day or every other day for a first period of time followed by a second period of time when no therapeutic units of the nonapeptide are administered to the human patient.

30. The method according to claim 29 wherein the first period of time is in the range of about 2 to 4 weeks, and the second period of time is in the range of about 2 to 5 weeks.

31. The method according to claim 30 wherein a cycle of administering the nonapeptide in isolated form for the first period of time followed by the second period of time when the nonapeptide is administered is repeated at least once.

32. The method according to claim 28 wherein the nonapeptide is formulated for oral administration.

* * * * *

UNITED STATES PATENT AND TRADEMARK OFFICE
CERTIFICATE OF CORRECTION

PATENT NO. : 6,852,700 B1
DATED : February 8, 2005
INVENTOR(S) : Marin Janusz et al.

It is certified that error appears in the above-identified patent and that said Letters Patent is hereby corrected as shown below:

Title page,
Item [73], Assignee, should read as follows:
-- Ludwik Hirszfeld Institute of Immunology and Experimental Therapy Polish Academy of Sciences, Wroclaw (PL); Georgiades Biotech Limited, Roadtown, Tortola (VG) --.

Signed and Sealed this

Fifteenth Day of November, 2005

JON W. DUDAS
*Director of the United States Patent and Trademark Office*